United States Patent [19]

Palermo et al.

[11] Patent Number: 5,350,397
[45] Date of Patent: Sep. 27, 1994

[54] AXIALLY DETACHABLE EMBOLIC COIL ASSEMBLY

[75] Inventors: Thomas J. Palermo, Palo Alto; Phong Pham, San Jose, both of Calif.

[73] Assignee: Target Therapeutics, Inc., Fremont, Calif.

[21] Appl. No.: 975,376

[22] Filed: Nov. 13, 1992

[51] Int. Cl.⁵ ............................................. A61M 29/00
[52] U.S. Cl. ................................. 606/200; 606/191; 606/108; 128/898
[58] Field of Search ............... 606/1, 108, 190, 194, 606/195, 198, 200; 604/11–15; 623/1; 128/898

[56] References Cited

U.S. PATENT DOCUMENTS

| | | |
|---|---|---|
| 3,334,629 | 8/1967 | Cohn . |
| 4,512,338 | 4/1985 | Balko et al. ........................ 606/108 |
| 4,739,768 | 4/1988 | Engelson . |
| 4,813,934 | 3/1989 | Engelson et al. . |
| 4,884,579 | 12/1989 | Engelson . |
| 4,957,501 | 9/1990 | Lahille et al. . |
| 4,994,069 | 2/1991 | Ritchart et al. . |
| 5,108,407 | 4/1992 | Geremia et al. . |
| 5,109,867 | 5/1992 | Twyford, Jr. . |
| 5,122,136 | 6/1992 | Guglielmi et al. . |
| 5,217,484 | 6/1993 | Marks ................................. 606/200 |

*Primary Examiner*—Stephen C. Pellegrino
*Assistant Examiner*—Glenn Dawson
*Attorney, Agent, or Firm*—Morrison & Foerster

[57] ABSTRACT

This invention is a surgical instrument and specifically is a device for delivering an embolic coil to a selected site within a vessel in a human body via use of a catheter. In particular, the device involves an embolic coil having an enlarged member, such as a ball attached thereto which coil is released by forcing the enlarged member through an aperture in a socket situated on the distal end of a pusher assembly.

7 Claims, 4 Drawing Sheets

AXIALLY DETACHABLE EMBOLIC COIL ASSEMBLY

FIELD OF THE INVENTION

This invention is a surgical instrument and specifically is a device for delivering embolic coils to a selected site within the vasculature of the human body via use of a catheter. In particular, the device involves an embolic coil having a radially enlarged member attached to one end, which coil is released by forcing the radially enlarged member axially through a distendible aperture situated on the distal end of a pusher assembly.

BACKGROUND OF THE INVENTION

The endovascular treatment of a variety of vascular maladies throughout the body is an increasingly more important form of therapy. Catheters have been used to place various treatment materials, devices, and drugs within arteries and veins in the human body. Examples of these devices and their use in such treatments are shown in U.S. Pat. application Nos. 07/806,898, now U.S. Pat. No. 5,234,437 ("Detachable Pusher-Vasoocclusive Coil Assembly with Threaded Coupling") and 07/806,912, Pending ("Detachable Pusher-Vasoocclusive Coil Assembly with Interlocking Ball and Keyway Coupling"). These show methods and devices for delivery of coils or wires within the human body to sites such as aneurysms, to occlude those sites. Coils such as are discussed in those two documents (as well as in U.S. Pat. No. 4,994,069), may be of a regular or helical configuration or may assume a random convoluted configuration at the site. The coils normally are made of a radiopaque, biocompatible metal such as platinum, gold, tungsten, or alloys of these and other metals. In treating aneurysms it is common to place a number of coils within the aneurysm. The coils occlude the site by posing a physical barrier to blood flow and by promoting thrombus formation at the site.

Coils have typically been placed at the desired site within the vasculature using a catheter and a pusher. The site is first accessed by the catheter. In treating peripheral or neural conditions requiring occlusion, the sites are accessed with flexible, small diameter catheters such as those shown in U.S. Pat. Nos. 4,739,768 and 4,813,934 may be used. The catheter may be guided to the site through the use of guidewires (see U.S. Pat. No. 4,884,579) or by the use flow-directed means such as balloons placed at the distal end of the catheter. Use of guidewires involves the placement of relatively long, torqueable proximal wire sections within the catheter attached to more flexible distal end wire sections designed to be advanced across sharp bends at vessel junctions. The guidewire is visible using x-ray and allows a catheter to be placed in vessels taking extremely tortuous paths, even when those vessel are surrounded by soft tissue such as the brain.

Once the chosen site has been reached, the catheter lumen is cleared by removing the guidewire (if a guidewire has been used), and the coil is placed into the proximal open end of the catheter and advanced through the catheter with a pusher. Pushers are wires having a distal end that is adapted to engage and push the coil through the catheter lumen as the pusher is advanced through the catheter. When the coil reaches the distal end of the catheter, it is discharged from the catheter by the pusher into the vascular site. This technique of discharging the coil from the distal end of the catheter has a number of undesirable limitations. First, because of the plunging action of the pusher and the coil, the positioning of the coil at the site cannot be controlled to a fine degree of accuracy. Second, once the coil has left the catheter, it is difficult to reposition or retrieve the coil if such is desired.

Several techniques have been developed to enable more accurate placement of coils within a vessel. In one technique (U.S. Pat. No. 5,122,136, issued Jun. 16, 1992) the coil is bonded via a metal-to-metal joint to the distal end of the pusher. The pusher and coil are made of dissimilar metals. The coil-carrying pusher is advanced through the catheter to the site and a low electrical current is passed through the pusher-coil assembly. The current causes the joint between the pusher and the coil to be severed via electrolysis. The pusher may then be retracted leaving the detached coil at an exact position within the vessel. In addition to enabling more accurate coil placement, the electric current may facilitate thrombus formation at the coil site. The only perceived disadvantage of this method is that the electrolytic release of the coil requires a period of time so that rapid detachment of the coil from the pusher does not occur.

Another technique for detaching an embolic coil is shown in U.S. patent application 07/806,912. In that document, a coil having an enlarged portion is mated with a pusher having a keyway adapted to receive the enlarged portion of the coil in an interlocking relationship. The junction between the pusher and the coil is covered by a coaxial member. The coaxial member is movable by sliding the member axially. As the coaxial member is moved away from the junction where the coil's member engages the keyway of the pusher, the coil disengages and the pusher may be removed.

Another device for placement of coils is shown in U.S. patent application 07/806,898. This device includes a coil having a helical portion at one end and a pusher which is threaded to the inside of the helical coil by the use of a threaded section on the outside of the pusher. The device operates to discharge the coil by engaging the proximal end of the coil with a sleeve while the pusher is unthreaded. Once the pusher is free, the sleeve may be used to push the coil out into the treatment area.

Another method of placing an embolic coil is shown in U.S. Pat. No. 5,108,407. This patent shows the use of a device in which embolic coils are separated from the distal end of a catheter by the use of heat-releasable adhesive bonds. The coil adheres to the therapeutic device via a mounting connection. Laser energy is transferred through a fiber optic cable which terminates at the connector. The connector becomes warm and releases the adhesive bond between the connector and the coil.

U.S. Pat. No. 3,334,629, to Cohn, suggests the use of a pusher having a socket to push an occlusive device within the inferior vena cava. However, the device's rounded end is not used to retain the occlusive device within the end of the inserter.

None of these disclosed devices suggest the use of a distendible aperture to precisely place embolic coils having the enlarged member on their ends within the vasculature by axially pressing the member through the aperture.

SUMMARY OF THE INVENTION

This invention is a device for placing detachable coils at a site within the vasculature of the human body so to occlude that site using the coils. The device includes a coil that carries an enlarged member (such as a ball or other rounded shape) at its proximal end; a pusher housing which has a distendible receiver, e.g., a socket, at its distal end having a throat or aperture which is smaller in diameter than the diameter of the member on the coil but which will distend to allow the ball to pass therethrough. The device also includes a plunger which is situated within the pusher housing and will press the coil's receiver through the distendible throat and thereby uncouple the coil from the pusher. This invention also includes the apparatus used to refit the distal end of the pusher with additional coils.

Another portion of the invention is a method for occluding a selected site within a vessel comprising the steps of: (a) accessing the site with a distal end of a catheter; (b) advancing the assembly described above through the catheter with the assembly situated at the proximal end of the pusher housing's throat to a position out the end of the distal end of the catheter; (c) activating the plunger to push the member axially through the distendible throat and thereby detach the coil from the pusher; and (d) withdrawing the catheter and pusher from the vessel. An alternative to step (d) may include the step of removing the pusher and reloading it with a coil while leaving the catheter in place.

Figure 1:
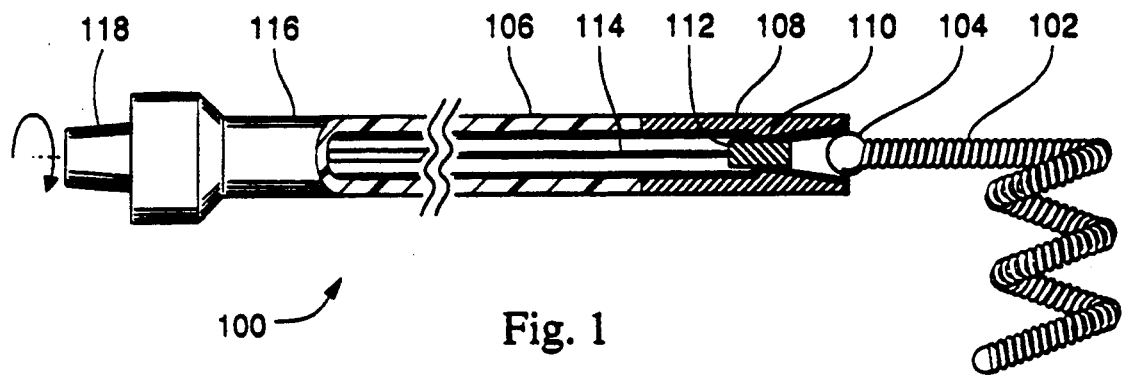
FIG. 1 is an enlarged, partial sectional view of the pusher-coil assembly showing the coil after uncoupling.

In the drawings, the following convention is used: the proximal end is to the left and the distal end is to the right.

DESCRIPTION OF THE INVENTION

One variation of the pusher-coil assembly (100) is shown in FIG. 1. The coil (102) is depicted to be helical in form, although it may be random or any other suitable form. The coil should be of a size sufficiently small that it may be advanced through a catheter that is appropriately sized for accessing the targeted vascular site. For instance, when accessing a brain aneurysm in a small vessel, an appropriately sized catheter is quite small and very flexible. The coil in such a situation must be small enough to fit through the catheter and out its distal end at the treatment site.

The coil is desirably made up of a radiopaque, physiologically compatible material. This material may be platinum, gold, tungsten, or alloys of these. A number of polymers are also suitable as coil material either alone or in conjunction with metallic markers providing radiopacity. These materials are chosen so that the process of locating the coils within the vessel may be viewed using radiography. However, it is also contemplated that these coils may be made of various other biologically inert polymers or of carbon fiber.

The size of the coil and its constituent winding will depend upon the use to which the coil will be placed. For occluding peripheral or neural sites, the coils will typically be made of 0.05 to 0.15 mm diameter wire (platinum or platinum/tungsten alloy) that is wound to have an inner diameter of 0.15 to 1.5 mm with a minimum pitch—that is to say that the pitch is equal to the diameter of the wire used in the coil. The length of the coil will normally be in the range of 0.5 to 60 cm, preferably 0.5 to 40 cm.

If desired, the coil may be formed in such a way that the coil is essentially linear as it passes through the catheter and yet assume a randomly oriented relaxed condition after it is released from the distal end of the catheter. A discussion of this variation may be found in U.S. Pat. No. 4,994,069.

Attached to coil (102) is a radially enlarged member, or ball (104). Ball (104) is firmly attached to coil (102) and should not separate during the installation treatment nor thereafter. The remainder of assembly (100) is made up of a pusher housing (106) which is a sheath or tube extending from the proximal end of the assembly (100) to the distal end terminated by a distendible aperture, a socket (108). Socket (108) includes a necked-down portion, a throat (110), which throat has a distendible aperture with a diameter smaller than that of ball (104). The ball (104) is pushed through throat (110) of socket (108) by a plunger head (112). Plunger head (112) easily fits within the aperture of throat (110) so to push ball (104) with its attached coil (102) out into the target site. The socket may have a constant inner diameter instead of the varying diameter shown in FIG. 1. Plunger head (112) is pushed via a pusher wire (114). Pusher wire (114) may, as is shown in FIG. 1, have a larger diameter at the proximal end of the assembly than at the distal end of the assembly near plunger head (112). In other variations, the diameter of pusher wire (114) may be constant throughout. The pusher wire (114) is desirably actuated by a screw-driven apparatus (116) and (118) in which as a knob (118) is rotated, the pusher wire (114) is advanced axially, distally down through the assembly (100) to push ball (104) out of the aperture (110) of socket (108).

The length of assembly (100) will be such as to be capable of being advanced entirely through the catheter to place coil (102) at the target site but yet with a sufficient portion of the proximal end of the assembly (100) protruding from the proximal end of the catheter to enable the plunger to be manipulated. For use in peripheral or neural surgeries, the pusher will normally about 100-200 cm in length, more normally 130-180 cm in length. The diameter of the pusher housing is usually in the range of 0.25 to about 0.90 mm.

Figure 2A:
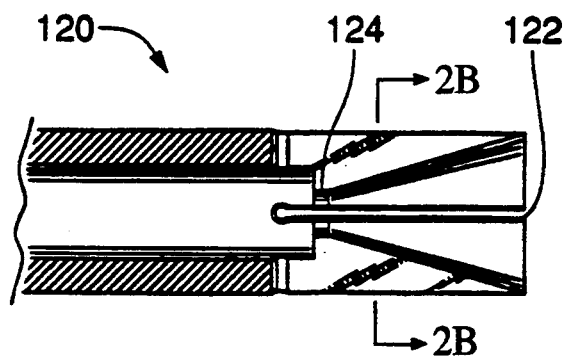
FIGS. 2A and 2B and 3A and 3B show variations of the tip of the socket on the pusher housing.
Figure 2B:
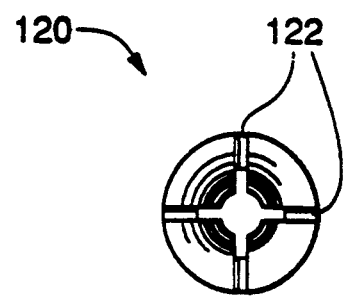
Figure 3A:
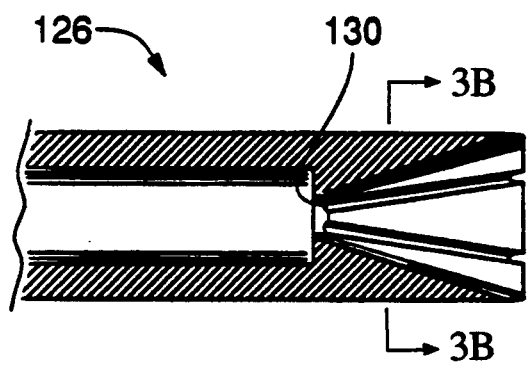
Figure 3B:
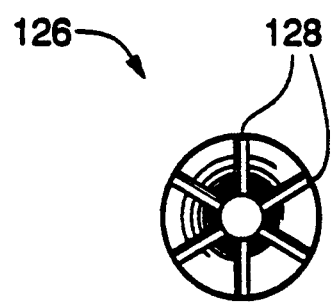

Two variations of the socket are shown are shown in FIGS. 2A and 2B and 3A and 3B. These variations are optional and are intended to lower the force needed to press ball (104) out through the throat of the socket aperture and yet hold the ball otherwise in a set position. In FIGS. 2A and 2B, socket (120) incorporates a number of slots (122) which extend through the wall of the socket and terminate down near the resting place of the ball. This variation allows the ball to be firmly held inside of the socket throat (124) and yet be ejected easily using the plunger apparatus shown in FIG. 1. FIG. 3A and 3B similarly show side cross-sectional views and end views of a socket which has grooves (128) cut from the distal end of the socket down into the aperture area (130). In each of FIGS. 2A and 2B and 3A and 3B, the respective throat diameters (124) and (130) are each smaller than the diameter of the ball which is placed through them.

Figure 4:
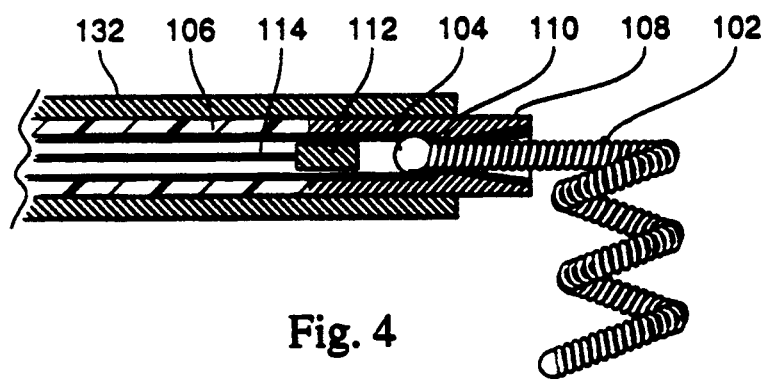
FIG. 4 is an enlarged view showing the distal end of the pusher housing, the plunger, and the ball on the coil engaged.

Assembly (100) is used to place one or more coils at the target site generally using the procedure as follows. As is shown in FIG. 4, the coil (102) with its attached ball (104) are included into socket (108) with the ball pushed past socket throat (110). Catheter (132) is inserted and navigated through to the chosen vessel site. The assembly (100) is then included into the catheter lumen to the site to be occluded.

Figure 5:
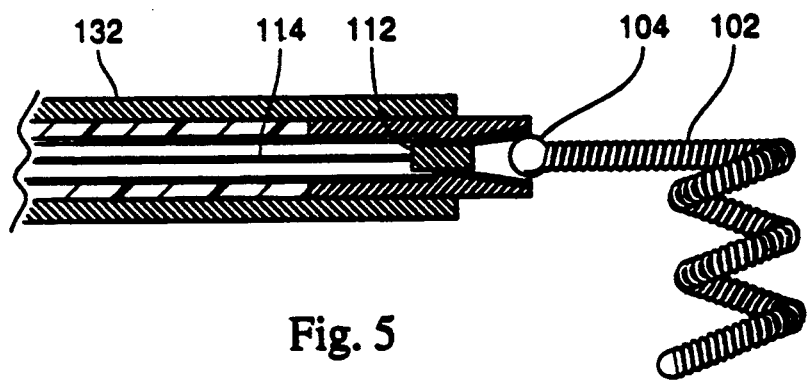
FIG. 5 is an enlarged view showing the distal end of the pusher housing, the plunger, and the ball on the coil not engaged.

As indicated previously, conventional catheter insertion and navigational techniques involving guidewires or flow-directed devices may be used to access the site with a catheter. Once the distal end of the catheter is positioned at the site, often by locating its distal end through the use of radiopaque materials of construction and radiography, the catheter is cleared. For instance, if a guidewire has been used to position the catheter, it is withdrawn from the catheter and then the assembly (100) is advanced through the catheter. The assembly (100) is advanced past the distal end of the catheter (132) so that the coil is free of the catheter and with the coil positioned precisely at the desired treatment site. As is shown in FIG. 5, plunger wire (114) is advanced to press the ball (104) and its attendant coil (102) into the target site. The entire catheter may then be removed or the assembly (100) may be withdrawn from the catheter lumen to provide for installation of other coils. If additional coils are to be placed at the target site, the procedure is repeated. After the desired number of coils have been placed at the site, the catheter is withdrawn from the vessel.

Figure 6:
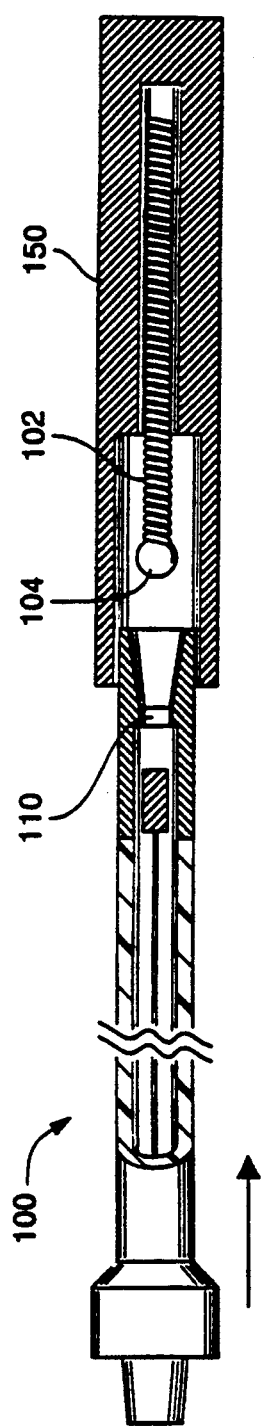
FIGS. 6, 7, and 8 show the procedure for reloading the pusher housing with another embolic coil.
Figure 7:
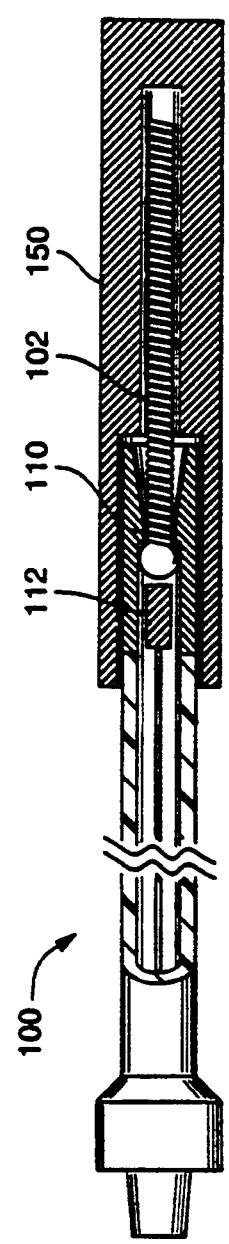
Figure 8:
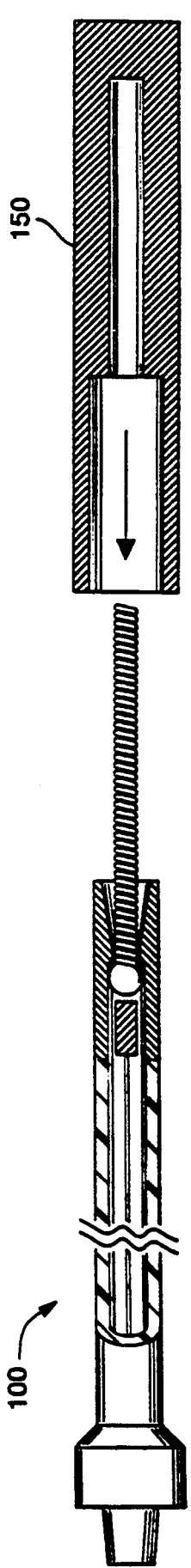

FIGS. 6, 7, and 8 show a method for reloading the assembly (100). FIG. 6 shows a coil introducer (150) which includes coil (102) and a ball (104). The coil introducer (150) is cylindrical and adapted to hold a coil (102) and a ball (104) in such a fashion as to allow entry of assembly (100) to one end and allow engagement of throat (110) over ball (104). As is shown in FIG. 7, the plunger head (112) is positioned out of the way as the ball is pressed through throat (110) into the position shown there. After the introduction of the ball (104) is complete, assembly (100) is withdrawn from coil introducer (150) as is shown in FIG. 8, then placed in a catheter lumen and passed axially along to the target site as described above.

Figure 9:
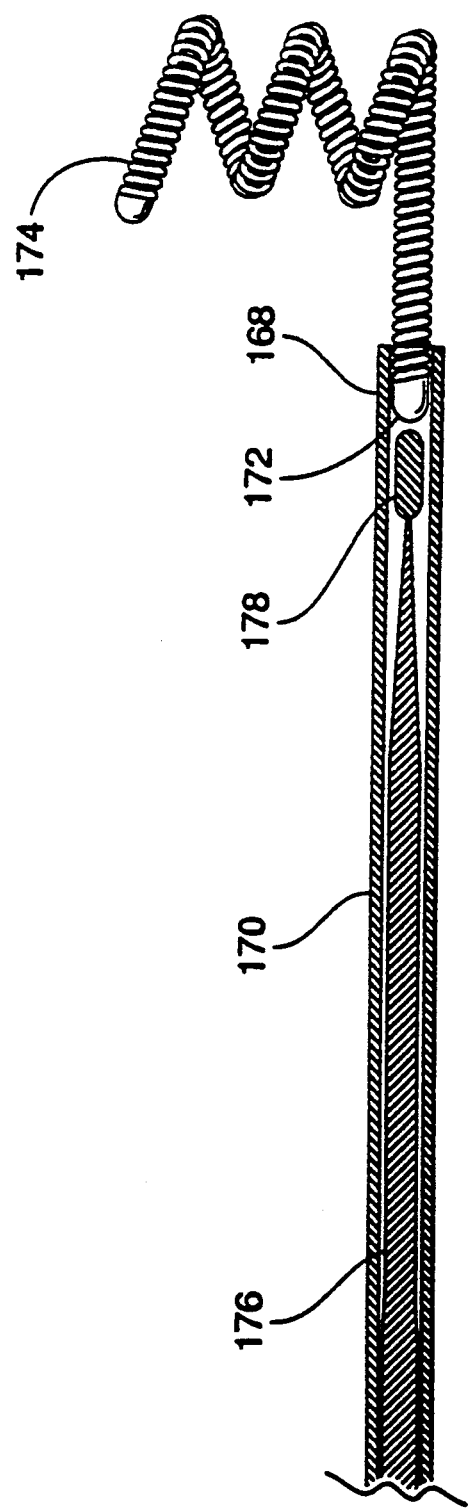
FIG. 9 shows a schematic side view of a variation of the invention using a tube aperture on the distal end of the pusher.

FIG. 9 shows a variation of the invention in which the distendible aperture at the distal end (168) of the pusher is of a relatively constant inside diameter. FIG. 9, the aperture is simply the end of a portion of tubing (170). The tubing (170) distal end (168) distends slightly as the enlarged member (172) attached to the end of coil (174) resides within.

In this variation, a guide wire (176) having a tip marker (170) to allow observation of the position of the tip of the guide wire in relation to the coil (174), is used as is the pusher in the variations noted above. The guide wire (170) is used to push the coil (174) with its enlarged member (172) axially through the tubing distal end (168). After such movement, the tubing distal end (168) returns to its original internal diameter.

Modifications of the device described above and methods of using it in keeping with this invention that are apparent to those having skill in this mechanical and surgical instrument design art and related fields are intended to be within the scope of the claims which follow.

I claim as my invention:

1. A pusher-coil assembly for use in occluding a selected site within a vessel comprising:
   (a) a vasoocclusive coil having a proximal end and a distal end and having an enlarged member with a diameter, said enlarged member fixedly attached to the coil's proximal end;
   (b) a pusher housing having a distal end and having a socket at its distal end, said socket having a throat aperture diameter smaller than the diameter of the enlarged member within which the enlarged member is held; and
   (c) a plunger located within the pusher housing, said plunger axially movable relative to the pusher housing and coil from a first position to a second position, which axial movement pushes the coil and the enlarged member through the socket throat and thus uncouple the coil from the pusher housing.

2. The assembly of claim 1 wherein the enlarged member is a ball.

3. The assembly of claim 1 wherein the vasoocclusive coil is selected from helical, random, or straight.

4. The assembly of claim 1 wherein the socket is slotted.

5. The assembly of claim 1 wherein the socket throat is grooved.

6. The assembly of claim 1 wherein the plunger comprises a plunger wire adapted to move axially within the pusher housing.

7. A method for occluding a selected site within a vessel comprising the steps of:
   (a) accessing the site with a distal end of a catheter;
   (b) advancing the assembly of claim 2 through the catheter until the ball attached to the coil is located distally of the distal end of the catheter;
   (c) pushing the plunger against the ball to detach the coil from the pusher housing; and
   (d) withdrawing the catheter from the vessel.

* * * * *